United States Patent
Saito et al.

(10) Patent No.: US 7,641,784 B2
(45) Date of Patent: Jan. 5, 2010

(54) METHOD FOR MEASURING BY MEANS OF CHEMICAL SENSOR, AND CHEMICAL SENSOR TYPE MEASURING APPARATUS

(75) Inventors: Soichi Saito, Tokyo (JP); Narushi Ito, Tokyo (JP)

(73) Assignee: Tanita Corporation, Tokyo (JP)

( * ) Notice: Subject to any disclaimer, the term of this patent is extended or adjusted under 35 U.S.C. 154(b) by 848 days.

(21) Appl. No.: 10/766,068

(22) Filed: Jan. 28, 2004

(65) Prior Publication Data

US 2004/0182723 A1 Sep. 23, 2004

(30) Foreign Application Priority Data

Jan. 30, 2003 (JP) ............... 2003-022070

(51) Int. Cl.
*G01N 27/327* (2006.01)
(52) U.S. Cl. ............... 205/775; 205/792; 204/402
(58) Field of Classification Search ........... 205/775, 205/792; 204/402, 403.09
See application file for complete search history.

(56) References Cited

U.S. PATENT DOCUMENTS

| | | | | |
|---|---|---|---|---|
| 4,734,184 A | * | 3/1988 | Burleigh et al. | 204/409 |
| 5,096,669 A | * | 3/1992 | Lauks et al. | 204/403.02 |
| 5,112,455 A | * | 5/1992 | Cozzette et al. | 205/778 |
| 5,352,349 A | * | 10/1994 | Inamoto et al. | 205/778 |
| 5,352,351 A | * | 10/1994 | White et al. | 204/403.04 |
| 5,411,647 A | * | 5/1995 | Johnson et al. | 205/777.5 |
| 5,795,774 A | * | 8/1998 | Matsumoto et al. | 204/403.11 |
| 6,599,473 B1 | | 7/2003 | Egger et al. | |
| 6,743,635 B2 | * | 6/2004 | Neel et al. | 436/95 |

FOREIGN PATENT DOCUMENTS

| | | |
|---|---|---|
| EP | 0 361 810 B1 | 12/1994 |
| EP | 0 626 577 B1 | 8/1998 |
| EP | 0 601 720 B1 | 1/2004 |
| EP | 1 051 621 B1 | 4/2005 |
| EP | 1 254 366 B1 | 5/2005 |
| JP | 57-60255 | 4/1982 |

(Continued)

*Primary Examiner*—Kaj K Olsen
(74) *Attorney, Agent, or Firm*—Knobbe Martens Olson & Bear LLP

(57) ABSTRACT

There is disclosed means for quickly solving instability of sensor sensitivity performances found in an initial stage and stabilizing the sensor sensitivity performances, when immersing a chemical sensor kept under a dry state in a buffer solution used as a storage liquid and applying a measurement bias between a working electrode and a reference electrode to make first use of the chemical sensor for measurement in which the chemical sensor is used. To make the first use of the chemical sensor, after immersing the chemical sensor kept under a dry state in the buffer solution used as the storage liquid, a first initial treatment bias having the same direction as that of the measurement bias and possessing an absolute value larger than that of the measurement bias is applied between the working electrode and the reference electrode for a first initial treatment time. Subsequently, the bias is changed to a second initial treatment bias which is the same as the measurement bias, and the second initial treatment bias is applied for a second initial treatment time. When such a two-step initial treatment operation is carried out, the stabilized sensor sensitivity performance is achieved.

18 Claims, 5 Drawing Sheets

FOREIGN PATENT DOCUMENTS

| | | |
|---|---|---|
| JP | 60-155959 | 8/1985 |
| JP | 63-122942 | 5/1988 |
| JP | 64-15649 | 1/1989 |
| JP | 64-23155 | 1/1989 |
| JP | 3-85435 | 4/1991 |
| JP | 7-49332 | 2/1995 |
| JP | 2000-162176 A | 6/2000 |

\* cited by examiner

◇ : 800mV, 1h + 700mV, 1h

□ : 700mV, 2h

△ : 800mV, 2h

Background Art

Background Art

METHOD FOR MEASURING BY MEANS OF CHEMICAL SENSOR, AND CHEMICAL SENSOR TYPE MEASURING APPARATUS

TECHNICAL FIELD

The present invention relates to a measuring method by means of a chemical sensor, and a chemical sensor type measuring apparatus based on the measuring method, more concretely to a measuring method by using an amperometric chemical sensor, and chemical sensor apparatus of an amperometric based on the measuring method, particularly to a measuring method by using an amperometric chemical sensor with use of an enzyme electrode as the amperometric chemical sensor therefor.

BACKGROUND ART

Examples of a method for measuring a concentration of a specific substance contained in a liquid sample include a method in which a current with oxidation or reduction of the specific substance is detected by using an electrochemical reaction, in particular a measuring method using an amperometric chemical sensor. In such a case, in actual, used is a method in which the concentration of the certain specific substance that is the measurement object is indirectly measured in such a manner that the action of an enzyme on a specific substance that is a measurement object is allowed to quantitatively produce an enzymatic reaction product thereof by the enzymatic reaction and the current associated with oxidation or reduction of the enzymatic reaction product is detected using the electrochemical reaction thereto. Concretely, an enzyme electrode including an enzyme film layer disposed on an electrode for use in the enzymatic reaction, for example, an immobilized enzyme electrode, in which an enzyme is immobilized on the electrode of platinum or carbon to form an immobilized enzyme film layer thereof, is used as the working electrode therein. A predetermined bias is applied between the working electrode and a reference electrode, and the electrochemical reaction to said product, which has been obtained from the specific substance contained in the liquid sample by the function of the enzymatic reaction, is initiated by the bias applied between the working electrode and the reference electrode so as to generate a current in quantitative relation with an amount of the enzymatic reaction product by using the electrochemical reaction.

The chemical sensor using the enzyme electrode is immersed in the liquid sample, usually, an aqueous solution sample for use. When the aqueous solution sample permeates and/or penetrates into enzyme film layer, a phenomenon in which foreign matters and impurities contaminating the sample are adsorbed on the surface of the enzyme film layer or a phenomenon in which the surface of the electrode underlying the enzyme film layer for the enzyme electrode is polluted or degenerated sometimes occurs. When the foreign matters or impurities are adsorbed on the surface of the enzyme film layer, it is a factor for lowering efficiency of the enzymatic reaction with the specific substance that is the measurement object. This is also a factor for gradually deteriorating a ratio of the current amount (sensor sensitivity) measured in relation to the specific substance concentration with an elapse of time. On the other hand, even when the efficiency of the enzymatic reaction is maintained, once the electrode surface has been contaminated and changed in properties, the efficiency of the electrochemical reaction for measuring the enzymatic reaction product is influenced thereby. As a result, it is another factor for deteriorating the ratio of the current amount (sensor sensitivity) measured in relation to the specific substance concentration with the elapse of time.

Various methods have been proposed as a method of recovering the sensor sensitivity drop occurring in course of usage of the amperometric chemical sensor using the above-described enzyme electrode, for example, induced by the contamination and degeneration of the surface of the electrode for use in the working electrode. One of the methods proposed is a method for the case that the amperometric chemical sensor using the enzyme electrode is used, wherein at every stage post to usage for some predetermined period, a bias in a direction reverse to that of the bias usually applied between the working electrode and a counter electrode at the time of measurement is applied between the working electrode and the counter electrode for a short time, and accordingly, the contamination and degeneration of the electrode surface are removed to reactivate the enzyme electrode; as being proposed in Japanese Patent Application Laid-Open Nos. 57-060255, 60-155959, and 1-15649.

Additionally, in such a method in which at every stage post to usage for some predetermined period, the bias in the reverse direction between the working electrode and the counter electrode is applied for the short time, in some case depending on a chosen level for the reverse bias applied, it leads to such condition that electrochemical generation of hydrogen gas is resulted in an aqueous buffer solution in which the chemical sensor is stored, and the fine hydrogen bubbles generated adhere on the surface of the electrode used as the working electrode for the enzyme electrode. Alternatively, an overcurrent sometimes flows through the electrodes. In such a case, the surface of the electrode for use in the working electrode is occasionally damaged by the overcurrent.

A method for improving various defects of the method in which the reverse bias is applied for the short time is also proposed in Japanese Patent Publication No. 4-54175 as the method for recovering the aforementioned sensitivity drop in the chemical sensor that is induced in association with the repeated measurements. In the method disclosed in the publication, for the amperometric chemical sensor using the enzyme electrode, triangular-wave bias sweeping is performed with respect to the bias applied between the working electrode (enzyme electrode) and the counter electrode after the measurement to reactivate the enzyme electrode. Accordingly, the improvement against the drop of the sensor sensitivity with the elapse of time is achieved.

For example, as shown in FIG. 8, as for a measurement system using a chemical sensor being composed of, in a cell 101 having an inflow port and outflow port, a working electrode 103 using an enzyme electrode comprising a Pt electrode on the surface of which an enzyme film 102 is immobilized, and a counter electrode 104 consisting of the Pt electrode, in a condition in which the cell 101 is filled with the buffer solution that does not contain a substrate for the enzymatic reaction, the bias is applied between the working electrode 103 and counter electrode 104, at the time of measurement, in such a manner that the counter electrode 104 is grounded, and a bias of +0.6 V set on the basis of a saturated calomel electrode (SCE) used as reference is applied for the working electrode 103. When a sample liquid is flowed through the cell 101 at a constant flow rate, an enzymatic reaction product is produced from a specific substance (enzyme substrate material) present in the sample liquid with the enzymatic reaction in the enzyme film 102, the enzymatic reaction product causes the electrochemical reaction, and a response current thereof flows in said applied bias. Since a difference between the response current and a basal current observed at the time of the flow of the buffer solution is proportional to an amount of the enzymatic reaction product, and thus is also proportional to the amount of the specific substance (enzyme substrate material) involved in the enzymatic reaction, the concentration of the specific substance (enzyme substrate material) present in the sample liquid is quantified based on a calibration curve prepared beforehand. After the measurement, the buffer solution is flushed in the cell 101 to wash up the cell. As a result, the enzyme electrode system returns to an initial state. When this operation for cleaning up is repeated, measurements for different sample liquids are repeatedly carried out.

When such repetition of measurement is progressed, components, having a comparatively high molecular weight, such as protein or lipid, which are other than the specific substance (enzyme substrate material) that is the measurement object, adhere slightly to the surface of the enzyme film layer. Moreover, components having a comparatively low molecular weight, such as low molecular weight amine or organic acid penetrate or permeate into the inside of the enzyme film layer, and are adsorbed on the electrode surface, or an oxide coat film is sometimes formed on the electrode surface. In the method proposed in the Japanese Patent Publication No. 4-54175, for example., when a platinum electrode is used both for the working electrode and counter electrode, the applied bias is swept repeatedly through such an applied bias range that electrolysis of water molecules or oxidation/reduction reaction of the components or a support electrolyte in the buffer solution does not occur in the buffer solution for use, for example, in a range of −0.5 V to +1.3 V (applied bias set on the basis of SCE), in such a manner that the applied bias is first increased to an upper limit bias from an applied bias of +0.6 V at the time of the measurement at a sweeping rate of 0.1 to 1 V/s, and then the applied bias is decreased to a lower limit bias, and thereafter the triangular wave bias sweeping is continued between the lower and upper limit bias for a certain duration. Finally, after repeating the triangular-wave bias sweeping, the triangular wave bias sweeping is ended at a time when the applied bias reaches +0.6 V that is the initial applied bias used for measurement. When a reactivating treatment of the enzyme electrode by the triangular wave bias sweeping is performed at every stage post to predetermined times of measurement, the sensor sensitivity that has dropped with the elapse of time is recovered. A state in which there is not any excessive drop of the sensor sensitivity can be maintained over a long period.

As shown in FIG. 9, when the triangular wave bias sweeping is performed between the upper and lower limit biases, and states in which forward/reverse bias is applied are alternately repeated, the components electrostatically adsorbed on the electrode surface at the time of the measurement are removed by switching of the bias. In addition, the oxide coat film formed on the platinum surface for use in the working electrode 103 is removed stepwise in course of repeating the states in which forward/reverse bias is applied alternatively.

DISCLOSURE OF INVENTION

The method of the reactivating treatment of the enzyme electrode is one of effective means for recovering the sensor sensitivity dropped with an elapse of time due to the repeated measurement. On the other hand, for the amperometric chemical sensor using the enzyme electrode, the enzyme film layer formed on the enzyme electrode in a preparation process is once brought into a dry state. At the stage of making first use of the sensor, the whole chemical sensor is immersed in the buffer solution to attain such a condition that the enzyme film layer is treated to damp and wet, and the buffer solution is charged between the surfaces of the working and reference electrodes. Then, a predetermined bias to be applied at the time of the measurement is applied between the working electrode and the reference electrode.

The present inventors have found that when the chemical sensor is set up at the stage of making first use thereof in the above-described procedure, an initial level of response current is low. When the predetermined bias for measurement is applied continuously for one to several days, a level of the response current gradually rises and reaches the constant level of a certain value. It is preferred that the initial instability of the sensor sensitivity generated immediately after the start of the use is solved by a simple operation to achieve quickly a desired level of sensor sensitivity, and this is a new problem which has not heretofore been recognized. Furthermore, it has been revealed that the initial instability of the sensor sensitivity is also found in common, for example, even in the amperometric chemical sensor in which a working electrode 2 and a reference electrode 4 are formed on an insulating substrate 1, an adhesive layer 6 capable of being impregnated with the solution is disposed to coat the surfaces of the both electrodes, and the enzyme electrode used therein is constituted with an enzyme film layer 5 being immobilized via the adhesive layer 6. Additionally, as shown in FIG. 5, in the case of the amperometric chemical sensor with use of the enzyme electrode being constituted in such a manner where inserted between the adhesive layer 6 and the enzyme film layer 5 is a selective permeation film 12 having a function of inhibiting permeation of low molecular compounds that causes an other electrochemical reaction than that of the enzymatic reaction product on the surface of the working electrode 2 and therefore acts as an interference component, and furthermore a limiting permeation film 11 having a function of limiting a permeation efficiency of the substrate compound which involves in the enzymatic reaction is disposed on the surface of the enzyme film layer 5, it has also been found that the initial instability of the sensor sensitivity is more remarkably observed.

The present invention is an approach for solving new problems described above, and an aim of the present invention is to provide a method for measuring a concentration of a specific substance contained in a liquid sample by means of a chemical sensor, particularly of an amperometric chemical sensor using an enzyme electrode, in which measuring method by the chemical sensor comprises, in the stage of carrying out an operation for making first use where the amperometric chemical sensor using an enzyme electrode kept in a dry state after prepared is immersed in a predetermined buffer solution, and a bias for measurement is then applied between a working electrode and a reference electrode therein, such an set-up operation step to start of use of the sensor being capable of simply solving an initial instability of sensor sensitivity in a short time and achieving a state indicating the stabilized sensor sensitivity with good reproducibility, and to also provide a chemical sensor type apparatus including a system adapted for said set-up operation step to start of use based on the measuring method.

The present inventors have proceeded with intensive studies to solve the above-described problems, and have confirmed that such phenomena as follows have been commonly observed to one degree or another for amperometric chemical sensors with use of an enzyme electrode having the same constitution used in such a conventional method; in the method choosing, as a treatment for initial setting up of the chemical sensor at the stage of making first use thereof, such a procedure that as an enzyme film layer formed on the enzyme electrode is brought in a dried state prior to the use of the amperometric chemical sensor with use of the enzyme electrode, at the stage of making first use of the sensor, the whole chemical sensor is first immersed in a buffer solution for use as a storage liquid at the time of standby to wet/treat the enzyme film layer and set a condition of the buffer solution being charged between the surfaces of a working electrode and a reference electrode, and thereafter a predetermined bias to be applied at the time of the measurement is applied between the working electrode and the reference electrode, found is such a phenomenon that a response current in early stage thereof is low, but when being held in a standby state in which the predetermined bias is applied continuously, the response current gradually rises within an elapse of one to several days and then reaches a constant level of a certain value in final. Moreover, as described above, by making a comparison between the amperometric chemical sensor with use of the enzyme electrode having such a constitution as shown in FIG. 1 and the amperometric chemical sensor with use of the enzyme electrode having such a constitution constituted as shown in FIG. 5, it has been confirmed that even though a initial drop amount of the sensor sensitivity thereof has a significant difference associated with the constitutions of the chemical sensors, such a tendency that the level of the response current gradually rises and reaches the constant level of a certain value while held in the standby state in which the predetermined bias is applied is highly common to the both two. That is, such a phenomenon has been revealed; while the whole amperometric chemical sensor with use of the enzyme electrode is brought in the dry state and stored under the atmospheric air until making first use thereof, a certain coat film layer is formed on the surface of a conductive material of the working electrode, and the drop of the sensor sensitivity caused by the coat film layer is observed in the early stage; however, while the sensor is held in the buffer solution in the state in which the predetermined bias for use in the measurement is applied continuously, the removing of the coat film layer formed on the surface of the conductive material is progressing favorably, which results in recovering of the sensor sensitivity from the dropped level to its standard level.

The present inventors further proceed with the study based on the findings. As a result, the present inventors has found that the process of removing the coat film layer formed on the surface of the conductive material has largely been promoted, as compared with the predetermined bias (bias in the forward direction) for use in the measurement, by applying a forward bias of further increased level to the sensor being held in the buffer solution. Additionally, it has been found that in such a case where after holding the sensor being applied with the forward-direction bias of such further increased level in the buffer solution for a certain time, and then the chemical sensor is placed at the use in the measurement immediately by setting the bias back to the predetermined bias used for the measurement, there are some occasions, depending on the circumstances therein, when the response current is raised up to the higher level than the targeted level of a specific value. Additionally, it has also been revealed that the targeted level of the specific value will be achieved, when the chemical sensor is placed at the use in the measurement after being held in the buffer solution for a specific time under such a condition that the applied bias is returned to the predetermined bias for use in the measurement. More concretely, the present inventors have confirmed advantages as follows; as the setting process of the chemical sensor at the stage for making first use thereof, when the amperometric chemical sensor with use of the enzyme electrode stored in the dry state is immersed in the buffer solution to wet/treat the enzyme film layer and set a condition of the buffer solution being filled at least between the surfaces of the working and reference electrodes thereof, and subsequently, the chemical sensor is held in the buffer solution under such a condition of a larger bias (in forward-direction) being applied between the working and reference electrodes as compared with the predetermined bias (in forward-direction) to be applied at the time of the measurement, the process of removing the coat film layer formed on the initial surface of the conductive material has largely been promoted; as a result, when treating for the predetermined time or more that is dependent on the higher value of the bias (in forward-direction) being initially applied, the removal of the coat film layer is totally accomplished. On the other hand, at such a case where a time for holding with the larger bias applied (in forward-direction) is excessive, when the chemical sensor is placed at use in the measurement immediately after the applied bias is returned to the predetermined bias for use in the measurement, such a phenomenon in which the level of the response current is conversely raised up to higher level than the targeted level of specific value is observed, but at such case when comprising a further step for holding the sensor in the buffer solution for a specific time under a condition that the applied bias is set again at the predetermined bias for use in the measurement, when the chemical sensor is placed at use in the measurement thereafter, the targeted level of the specific value is obtained for the response current of the chemical sensor in the measurement.

Furthermore, the present inventors have also found that the phenomenon in which the chemical sensor sensitivity gradually drops still occurs, in the course of ordinary use where the measurements are repeated by using the amperometric chemical sensor with use of the enzyme electrode after ending the treatment process for setting up the chemical sensor at the stage of making first use thereof, and as for the sensor sensitivity drop resulted from the repeated measurement, when such a treatment is performed in which the chemical sensor is held first for the specific duration under the condition that while being immersed in the buffer solution, the raised bias in the forward-direction is applied thereto as compared with the predetermined bias (bias in the forward direction) for use in the measurement, and sequentially the chemical sensor is held for a certain time with the applied bias being set back to the predetermined bias (the bias in the forward direction), the lowered sensor sensitivity can be recovered thereby.

The present inventors have completed the present invention based on the series of findings described above. That is, there is provided a measuring method by means of a chemical sensor, according to the first aspect of the present invention, which is a method of measuring a concentration of a specific substance contained in a measurement sample by use of a chemical sensor comprising at least a working electrode and a reference electrode, wherein the method is a measurement method according to such a procedure that the chemical sensor is immersed into a buffer solution of a predetermined composition used as a storage liquid during standby, and a predetermined measurement bias is applied between the working electrode and the reference electrode to hold the chemical sensor in the buffer solution, and the chemical sensor is immersed into the measurement sample instead of the buffer solution, and the measurement bias applied between the working electrode and the reference electrode is used to measure the concentration of the specific substance contained in the measurement sample based on a change in an amount of a current produced by an electrochemical reaction during measurement; and the method comprising, at the stage of making first use of the chemical sensor, after immersing the chemical sensor kept under a dry state into the buffer solution to bring the surfaces of the working electrode and reference electrode into contact with the buffer solution;

a first initial treatment step of applying a first initial treatment bias having the same direction as that of the measurement bias and possessing an absolute value larger than that of the measurement bias between the working electrode and the reference electrode to hold the chemical sensor in the buffer solution for a predetermined first initial treatment time;

a second initial treatment step of changing the bias to be applied between the working electrode and a reference electrode to a second initial treatment bias which is the same as the measurement bias, after ending the first initial treatment step, while the chemical sensor is immersed in the buffer solution, and holding the chemical sensor in a standby state; and after the completion of the second initial treatment step, the chemical sensor is placed for the first time at the use for measurement of the measurement sample. In said process, it is preferred that after ending the first initial treatment step, in the second initial treatment step, the chemical sensor is held in the standby state for a predetermined second initial treatment time.

Additionally, in the measuring method by using the chemical sensor according to the first aspect of the present invention, the method is preferably carried out in such a manner where the chemical sensor further comprises the counter electrode in addition to the working electrode and the reference electrode, the reference electrode is constituted of a material having a predetermined chemical potential difference from the working electrode, when brought into contact with the buffer solution, the reference electrode is used as a reference to set the bias for the working electrode in such a manner that a desired bias is applied between the working electrode and the reference electrode, and the steps of applying the measurement bias, the first initial treatment bias, and the second initial treatment bias are set respectively in such a manner that the difference between the biases of the reference electrode and working electrode in the buffer solution imparts the bias difference in accordance with the measurement bias, the first initial treatment bias, and the second initial treatment bias.

In said case, for example, it is desirable that a silver/silver chloride electrode is used as the reference electrode, and a platinum electrode is used for the working electrode and the counter electrode therein, and said measurement bias applied between the working electrode and the reference electrode during the measurement is an applied bias obtained by the bias of the working electrode selected from a range of 400 to 700 mV on the datum basis of the silver/silver chloride electrode used as the reference electrode in the buffer solution.

Alternatively, it is preferred that in the first initial treatment step, an applied bias at which an electrolysis reaction of water starts on the working electrode and the reference electrode in the buffer solution is defined as an applied bias upper limit value, and the measurement bias is defined as an applied bias lower limit value on the datum basis of the silver/silver chloride electrode used as the reference electrode, respectively; and by using an upper/lower limit bias difference defined by a difference between the applied bias upper and lower limit values, the first initial treatment bias applied between the working electrode and the reference electrode is selected in a range of the applied bias which is larger than the measurement bias by 10% or more of the upper/lower limit bias difference and which is smaller than the applied bias upper limit value by at least 200 mV or more.

Furthermore, it is also preferable that in the case where a silver/silver chloride electrode is used as the reference electrode, and a platinum electrode is used for the working electrode and the counter electrode;

in the first initial treatment step, the first initial treatment bias applied between the working electrode and the reference electrode is selected in a range of the applied bias which is larger than the measurement bias by at least 100 mV or more and which does not exceed 900 mV on the datum basis of the silver/silver chloride electrode used as the reference electrode in the buffer solution.

For example, it is more preferable that in the case where a silver/silver chloride electrode is used as the reference electrode, and a platinum electrode is used for the working electrode and the counter electrode;

in the first initial treatment step, the first initial treatment bias applied between the working electrode and the reference electrode is selected in a range of at least 750 mV to 900 mV on the datum basis of the silver/silver chloride electrode used as the reference electrode in the buffer solution, and the first initial treatment time is selected in a range of four hours or less and at least not less than one hour. On the other hand, it is desirable that said second initial treatment time is selected at least in a range of not less than one hour. Additionally, it is more desirable that a total of the first initial treatment time and the second initial treatment time is selected in a range of six hours or less.

It is to be noted that in the measuring method by means of the chemical sensor according to the first aspect of the present invention, it is more preferable that said chemical sensor is an amperometric chemical sensor which has three electrodes including the counter electrode in addition to the working electrode and the reference electrode, wherein the working electrode, counter electrode, and reference electrode are all formed on an insulating substrate, and an enzyme electrode comprising at least an immobilized enzyme film layer disposed on the surface of the working electrode is used for the current detection.

Furthermore, there is provided a measuring method by means of a chemical sensor, according to the second aspect of the present invention, which is a method of measuring a concentration of a specific substance contained in a measurement sample by use of a chemical sensor having at least a working electrode and a reference electrode, wherein the method is a measurement method according to such a procedure that the chemical sensor is immersed into a buffer solution of a predetermined composition used as a storage liquid during standby, and a predetermined measurement bias is applied between the working electrode and the reference electrode to hold the chemical sensor in the buffer solution, and the chemical sensor is immersed into the measurement sample instead of the buffer solution, and the measurement bias applied between the working electrode and the reference electrode is used to measure the concentration of the specific substance contained in the measurement sample based on a change in an amount of a current produced by an electrochemical reaction during measurement; and the method comprising, at every stage post to continued use of the chemical sensor for a predetermined period, in a condition in which the chemical sensor in a standby state is immersed in the buffer solution, and the surfaces of the working electrode and reference electrode are allowed to contact the buffer solution;

a first refresh treatment step of applying a first refresh treatment bias having the same direction as that of the measurement bias and possessing an absolute value larger than that of the measurement bias between the working electrode and the reference electrode, and holding the chemical sensor in the buffer solution for a predetermined first refresh treatment time;

a refresh standby treatment step of changing the bias applied between the working electrode and the reference electrode to a second refresh treatment bias which is the same as the measurement bias, after ending the first refresh treatment step, while the chemical sensor is immersed in the buffer solution, and holding the chemical sensor in a standby state for a second refresh treatment time; and after completion of the refresh standby treatment step, the chemical sensor is placed again at the use for the measurement of the measurement sample.

On the other hand, there is also provided a chemical sensor type measuring apparatus of the present invention which is suitable for carrying out the measuring method by using the chemical sensor according to the present invention, as defined above, that is, the chemical sensor type measuring apparatus according to the first aspect of the present invention is a chemical sensor type measuring apparatus being capable of measuring operation in accordance with the aforementioned measuring method by use of a chemical sensor according to the first aspect of the present invention, the apparatus comprising:

a chemical sensor having at least a working electrode and a reference electrode;

a signal detection circuit including at least means for applying a bias between the working electrode and the reference electrode, and means for detecting a signal measured by the chemical sensor; and the apparatus further comprising a notification device used at the stage of making first use of the chemical sensor, wherein the notification device comprising:

a system for applying a first initial treatment bias having the same direction as that of the measurement bias and possessing an absolute value larger than that of the measurement bias between the working electrode and the reference electrode for a predetermined first initial treatment time in a condition in which the chemical sensor kept under a dry state is immersed in a buffer solution to allow the surfaces of the working electrode and the reference electrode to contact the buffer solution at the stage of making first use of the chemical sensor;

a system for changing the bias to be applied between the working electrode and the reference electrode to a second initial treatment bias which is the same as the measurement bias to apply the second initial treatment bias for a second initial treatment time, while the chemical sensor is continuously immersed in the buffer solution; and a system for notifying that the chemical sensor is ready to apply for measurement thereafter at the time of end of said two-step initial treatment operation.

Furthermore, there is provided a chemical sensor type measuring apparatus according to the second aspect of the present invention, which is a chemical sensor type measuring apparatus being capable of measuring operation in accordance with the aforementioned measuring method by use of a chemical sensor according to the second aspect of the invention, the apparatus comprising:

in which a measuring operation is possible in accordance with the measuring method by a chemical sensor according to claim 11, the apparatus comprising:

the chemical sensor having at least a working electrode and a reference electrode;

a signal detection circuit including at least means for applying a bias between the working electrode and the reference electrode, and means for detecting a signal measured by the chemical sensor; and the apparatus further comprising a notification device used at every stage post to continued use of the chemical sensor for a predetermined period, wherein the notification device comprising:

a system for applying a first refresh treatment bias having the same direction as that of the measurement bias and possessing an absolute value larger than that of the measurement bias between the working electrode and the reference electrode for a first refresh treatment time in a condition in which the chemical sensor in a standby state is immersed in the buffer solution, and the surfaces of the working electrode and reference electrode are allowed to contact a buffer solution every use of the chemical sensor for a predetermined period;

a system for changing the bias applied between the working electrode and the reference electrode to a second refresh treatment bias which is the same as the measurement bias, and applying the second refresh treatment bias for a second refresh treatment time, while the chemical sensor is continuously immersed in the buffer solution; and a system for notifying that that the chemical sensor is ready to apply again for measurement thereafter at the time of end of said two-step refresh treatment operation.

BEST MODE FOR CARRYING OUT THE INVENTION

Next, the present invention will be described in more detail with reference to the drawings.

First Embodiment

Figure 1:
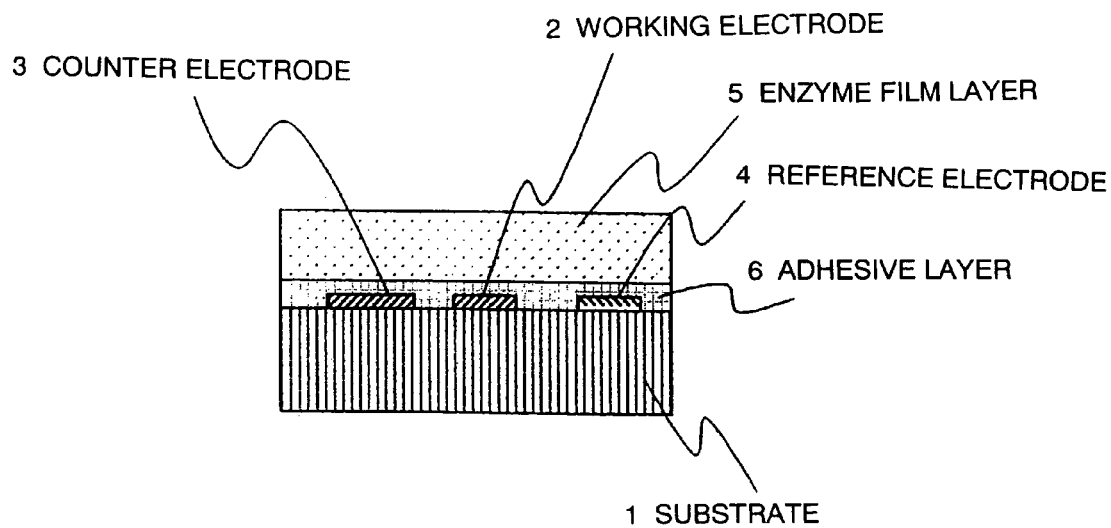
FIG. 1 is a sectional view schematically showing one example of a chemical sensor constitution using an enzyme electrode for use in the first embodiment of the present invention.

FIG. 1 is a sectional view schematically showing one example of a chemical sensor constitution for use in a first embodiment of the present invention. The chemical sensor as shown in FIG. 1 is constituted of a three electrodes type chemical sensor, and a working electrode 2 and counter electrode 3 constituted of conductors, and a reference electrode 4 are formed on an insulating substrate 1. An enzyme film 5 is formed on an electrode system of the three electrodes type, and is constituted as a so-called enzyme electrode type chemical sensor. It is to be noted that in the enzyme electrode, an adhesive layer 6 is disposed between the electrode system and the enzyme film 5 in order to immobilize the enzyme film 5. The insulating substrate 1 does not indicate permeability to liquid, and the electrode system contacts the liquid via the enzyme film 5 and adhesive layer 6 which have the permeability to liquid.

In this type of chemical sensor, signals such as currents to be measured are detected in a state in which a predetermined bias is applied between the respective electrodes of the three electrodes type. Therefore, the sensor is incorporated in a sensor cartridge including a lead terminal for each electrode. After preparing the chemical sensor and performing a predetermined operation characteristic inspection, the sensor is dried, sealed in an airtight package (bag material) together with a drying agent in order to prevent the enzyme film 5 or the adhesive layer 6 from absorbing unnecessary humidity (moisture), and brought into a circulation process.

When a user uses an enzyme electrode type chemical sensor sealed in the package, first the package is opened, and electrode terminals disposed corresponding to each other are connected to each other between the enzyme electrode type chemical sensor and a measuring circuit. Next, the enzyme electrode type chemical sensor is immersed in a storage liquid in a state in which the bias is not applied. A buffer solution having a specific composition is usually used as this storage liquid. When immersed into the buffer solution used as the storage liquid, the enzyme film 5 and adhesive layer 6 kept under a dry state are impregnated with the solution, and changed into a wet state. At this time, for example, with permeation of the solution, the enzyme film 5 is recovered to an originally swollen layer from an evaporated state. From a microscopic point of view, for enzyme protein constituting the enzyme film 5, and organic materials such as a matrix material for immobilizing the film, a coupling state among molecules, relative arrangement among the molecules, and alignment slightly change in accordance with a degree of permeation of the buffer solution.

Next, when the whole surfaces of the working electrode 2, counter electrode 3, and reference electrode 4 contact the buffer solution penetrated and filled in the adhesive layer 6, a predetermined bias is applied to the electrode system. When the bias is applied between the working electrode 2 formed of conductors such as a platinum electrode and the reference electrode 4 constituted of silver/silver chloride, the working electrode 2 and reference electrode 4 constitute a capacitor via the buffer solution functioning as an electrolytic solution. As a result, a process of electrically charging the capacitor occurs, and electric charges are accumulated on the surface of the working electrode to form electric double layers. An induced current flows in a pulse manner immediately after application of the bias. Thereafter, the current decreases to a remarkably weak current, and a transitional time of about several minutes is required until the current becomes constant.

In this case, when a surface coat layer formed of a dielectric material exists on the surface of the working electrode 2 formed of conductors such as a platinum electrode, a reaction efficiency of an electrochemical reaction in this chemical sensor also depends, for example, on efficiency of injection of the electric charges onto the surface contacting the solution from the working electrode 2 through the surface coat layer, and is therefore influenced by the thickness and presence/absence of the surface coat layer. Therefore, if the thickness and microscopic composition of the surface coat layer formed on the surface of the working electrode 2 differ from those of the surface coat layer in a "stationary state" achieved in stably holding the enzyme electrode type chemical sensor in a standby state in the enzyme electrode type chemical sensor stored in the dry state, the reaction efficiency of the electrochemical reaction in the chemical sensor deviates from that in the "stationary state" immediately after the start of the use. While the bias in the standby state continues to be applied, the reaction for the gradual change into the thickness and microscopic composition of the surface coat layer in the "stationary state" occurs in the surface of the working electrode.

It is presumed that instability of sensor sensitivity performances found in an initial stage at the start of the use of the chemical sensor reflects the above-described transitional phenomenon. That is, details of the electrochemical reaction in an interface for changing microscopic conditions of the surfaces of the working electrode 2 and reference electrode 4 in the enzyme electrode type chemical sensor stored in the dry state to those of the surface of the working electrode 2 in the "stationary state" have not been clarified yet. However, it has been confirmed that the reaction proceeds by at least the bias (bias of the forward direction) having the same direction as that of the measurement bias applied between the working electrode 2 and the reference electrode 4 even in the standby state. Additionally, when the bias (forward-direction bias) having the same direction as that of the measurement bias and possessing an absolute value larger than that of the measurement bias is applied, an electrochemical reaction rate in the interface is rapidly promoted.

Additionally, when the bias applied between the working electrode 2 and the reference electrode 4 is excessively increased, an oxidation/reduction reaction starts in the surface of the electrode in the used buffer solution in accordance with a type of solvent, buffer solution components, and support electrolyte. That is, the applied bias needs to be selected in a range (referred to as so-called "bias window region") in which an unnecessary electrochemical reaction coming from the used buffer solution does not occur. Furthermore, with the application of the bias which does not reach the upper limit of the "bias window region" but has a large bias in the forward direction between the working electrode 2 and the reference electrode 4, a micro current flowing between the working electrode 2 and the reference electrode 4 constitutes a "dark current", rapidly increases, and sometimes causes operation defect of the enzyme electrode type chemical sensor, and deficit of the enzyme film layer.

In the measuring method by the first chemical sensor according to the present invention, in order to quickly change the microscopic conditions of the surfaces of the working electrode 2 and reference electrode 4 to those of the surfaces of the working electrode 2 and reference electrode 4 in the "stationary state" in the enzyme electrode type chemical sensor stored in the dry state, the sensor is immersed into the buffer solution used as the storage liquid. Thereafter, first the bias (first initial treatment bias) having the same direction as that of the measurement bias (forward-direction bias) and possessing an absolute value larger than that of the measurement bias is applied. The electrochemical reaction rate in the interface is rapidly promoted. For example, the reaction requiring one to three days can be achieved in the first initial treatment time selected within four hours in the standby state in which the measurement bias is applied, while the first initial treatment bias is applied for the first initial treatment time. Thereafter, the bias applied between the working electrode 2 and the reference electrode 4 is changed to the second initial treatment bias which is the same as the measurement bias, and the second initial treatment bias is applied. Then, the amount of charges accumulated on the opposite electrode surfaces of the working electrode 2 and reference electrode 4 to form the electric double layer when applying the first initial treatment bias is decreased to that to be accumulated in a state in which the second initial treatment bias (measurement bias) is applied. A discharge process of the electrode is completed in a short time in the same manner as in the charge process. On the other hand, for the enzyme film 5 and adhesive layer 6 in addition to the electric double layer by the charges accumulated on the surfaces of the opposite electrodes, the change induced by an electrostatic field needs to be recovered. Since the recovery of the electrostatic change caused in the enzyme film 5 and adhesive layer 6 more moderately proceeds, the time for applying and holding the second initial treatment bias (measurement bias) is preferably set in completion of the shifting to a state similar to that at the standby time in the targeted "stationary state" in the whole enzyme electrode type chemical sensor.

Even if the second initial treatment is shortened, major factors of the instability of the sensor sensitivity performances found in the initial stage of the start of the use of the chemical sensor are removed in the first initial treatment step. There is a possibility of deviation from the stable measurement result of the targeted "stationary state" in the measurement performed immediately after the step. However, the chemical sensor is held in a state in which the second initial treatment bias (measurement bias) is applied, corresponding to the second initial treatment step, while holding the standby state before the second measurement is performed.

In the chemical sensor of the three electrodes type shown in FIG. 1, a silver/silver chloride electrode is used as the reference electrode 4. When the working electrode 2 and counter electrode 3 are formed by a platinum electrode, the range referred to as the "bias window region" corresponds to a range of the bias of the working electrode 2 set to −0.6 V to 1.2 V on the basis of the silver/silver chloride electrode constituting the reference electrode 4. It is to be noted that as the storage liquid for use, buffer solutions in a neutral state such as N-tris-(hydroxymethyl)methyl-2-aminoethanesulfonic acid (TES) containing 150 mM of sodium chloride, and a buffer solution of pH 7 can be used.

The storage liquid suitable for the enzyme electrode type chemical sensor is a buffer solution in which enzyme activity of a used enzyme protein can be held, and usually contains a support electrolyte selected from sodium chloride, potassium chloride, and calcium chloride, and a buffer agent component in which a desired pH is maintained. As the buffer agent components, a maintained pH value is selected also in consideration of an indicated pH of the enzyme for use. In many cases, a general phosphoric buffer solution, or a group of good buffer solutions for use in various enzymatic reactions such as an aminopropane sulfonic acid derivative (MOPS, etc.), an aminoethane sulfonic acid derivative (MES, etc.), HEPES, and PIPES can be used.

A buffer solution having a small base current flowing through the chemical sensor in the standby state is usually selected in the storage liquid, and the electrode of the chemical sensor is accordingly inhibited from being deteriorated. On the other hand, in the initial treatment operation of the present invention, the bias to be applied between the working electrode and the reference electrode is increased, and the amount of the current injected into the buffer solution from the electrode is remarkably increased. In a mechanism in which the process of removing the surface coat film disposed on the electrode surface is accordingly accelerated, with the use of a buffer solution having a higher increase ratio of the injected current, there is an effect of further acceleration of the process of removing the surface coat film. When the same bias to be applied between the working electrode and the reference electrode is set, even with the buffer solution maintaining the same pH value, a difference is sometimes made in the amount of the current injected into the buffer solution from the electrode depending on the buffer agent components. For example, chemical materials for use in buffer agent components have molecular shapes or sizes by which electrons are easily transmitted/received with respect to the electrode or by which the surface of the electrode is easily accessible. Then, the increase of the amount of the current injected to the buffer solution from the electrode via the electron transmission/reception with respect to the chemical substance is anticipated. In accordance with the present inventors' study, concretely there is an effect that the base current is increased in a (2-hydroxyethyl)imino-tris-(hydroxymethyl)methane buffer solution (Bi-Tr, Bis). For example, in the enzyme electrode type chemical sensor described later in Example 1, for the measurement bias, when 0.1 M Bi-Tr, Bis, 0.15 M NaCl, pH 7 is used as a storage liquid composition in applying a bias of 0.45 V to the working electrode, a larger amount of base current in the standby state by about 10 nA is generated as compared with the use of a TES buffer solution containing 150 mM of sodium chloride.

For example, when the working electrode 2 and counter electrode 3 are formed by platinum electrodes, the bias of the working electrode 2 at which the electrochemical reaction of hydrogen peroxide added into the buffer solution starts is about 350 mV on the basis of the silver/silver chloride electrode constituting the reference electrode. When the enzyme electrode type chemical sensor shown in FIG. 1 includes a system for measuring hydrogen peroxide generated by the enzymatic reaction from glucose of the substrate by glucose oxidase enzyme, for the measurement bias, the bias of the working electrode 2 is set in a range of 400 mV to 700 mV on the basis of the silver/silver chloride electrode constituting the reference electrode. In the response current generation accompanying the electrochemical reaction of hydrogen peroxide, a maximum efficiency is indicated in the vicinity of 700 mV. However, influences of interference components such as vitamin C (ascorbic acid) rapidly increase, when the bias of the working electrode 2 is selected at 700 mV or more. In consideration of this respect, the above-described range is preferable as the measurement bias.

On the other hand, in the first initial treatment step, the first initial treatment bias applied between the working electrode 2 and reference electrode 4 is preferably selected as a value significantly larger than that of the measurement bias. Therefore, when the silver/silver chloride electrode is used as the reference electrode, and the working electrode and counter electrode are formed of the platinum electrodes, the first initial treatment bias is preferably selected in such a range that the bias is larger than the measurement bias by at least 100 mV or more and does not exceed 900 mV on the basis of the silver/silver chloride electrode constituting the reference electrode in the buffer solution. For example, the bias of the working electrode 2 is selected in a range of at least 750 mV to 900 mV, and the first initial treatment time is selected in a range of four hours or less, not less than at least one hour on the basis of the silver/silver chloride electrode constituting the reference electrode in the buffer solution.

Thereafter, a time for which the applied bias is changed and the second initial treatment bias (measurement bias) is applied and held (second initial treatment time) is preferably set to be gradually longer with increases of the bias change amounts of the first initial treatment bias and the second initial treatment bias (measurement bias). However, the bias application direction is not reversed at the time of the bias change, the bias change amount is about 500 mV at most, and a sufficiently stable state can be achieved in a second initial treatment time of one hour or less.

These procedures are stored in software of the measuring apparatus main body using the enzyme electrode type chemical sensor. When a series of initial treatment operations are completed, and the standby state held at the measurement bias is achieved, a notification device can be allowed to notify that the measurement is possible. It is to be noted that as notifying means, displays such as LCD, sound, vibration, and the like may also be used. When a mechanism for the measuring apparatus using the enzyme electrode type chemical sensor is added beforehand, a user can connect the apparatus to a new sensor cartridge and perform a measurement with good reproducibility in a first measurement.

It is to be noted that in the above description, the procedure in the enzyme electrode type chemical sensor has been described. However, a similar method can also be applied to chemical sensors such as a lactic acid sensor, and a hydrogen peroxide sensor using a selective permeation film formed of an organic material. Furthermore, even when the bias of the working electrode is set as the measurement bias on a negative side as in an oxygen sensor, the present invention can also be applied using the bias having the same application direction as that of the measurement bias and possessing a larger absolute value.

EXAMPLE 1

A glucose sensor constituted as shown in FIG. 1 was used as the enzyme electrode type chemical sensor. An electrode system of the enzyme electrode type chemical sensor was set to a three electrodes type constituted of the working electrode 2 and counter electrode 3 of Pt, and the reference electrode 4 of Ag/AgCl. The enzyme film 5 was formed by immobilizing glucose oxidase in a matrix of albumin and glutaric aldehyde. A silane coupling agent was disposed as the adhesive layer 6 between the enzyme film 5 and the electrode. The enzyme electrode type chemical sensor was sealed in a cartridge 7 formed of plastic in a liquid-tight manner and was used. A window 8 was disposed in the cartridge 7 so that only a sensitive portion of the glucose sensor contacts the solution. Thereafter, unless especially mentioned, it is defined that the cartridge 7 includes the enzyme electrode type chemical sensor.

Figure 2:
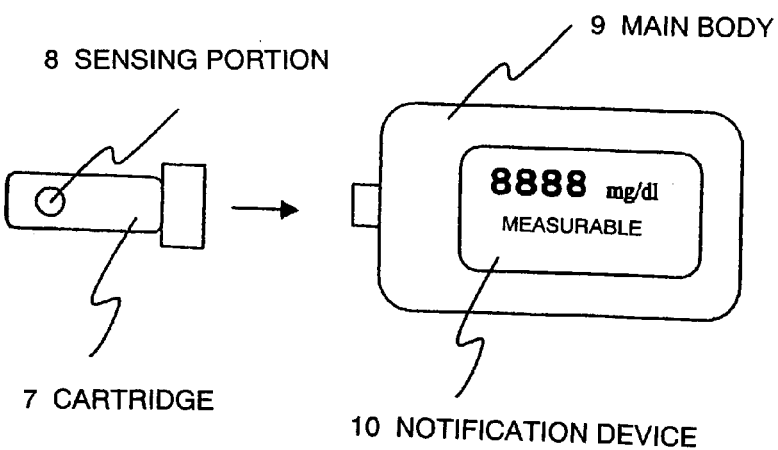
FIG. 2 is a diagram schematically showing a whole constitution of a usable chemical sensor type measuring apparatus main body and a chemical sensor portion cartridge in the first to third embodiments of the present invention.

In the present example, a main body 9 designed as a measuring circuit exclusive for the glucose sensor including the three electrodes type is used. In the main body 9, a potentiostatic circuit for supplying a predetermined constant bias to the working electrode 2 and a measuring circuit therewith as well as a notification device 10 is disposed. FIG. 2 shows a schematic appearance diagram of the measuring apparatus.

The measurement was performed as follows. First, the cartridge 7 stored in the dry state for one year was taken out together with a drying agent, and connected to the main body 9. Next, the cartridge was immersed in the storage liquid so that the sensitive portion contacted the liquid. It is to be noted that the used storage liquid is a buffer solution of N-tris-(hydroxymethyl).methyl.2-aminoethanesulfonic acid (TES) containing 150 mM of sodium chloride at pH 7.

Figure 3:
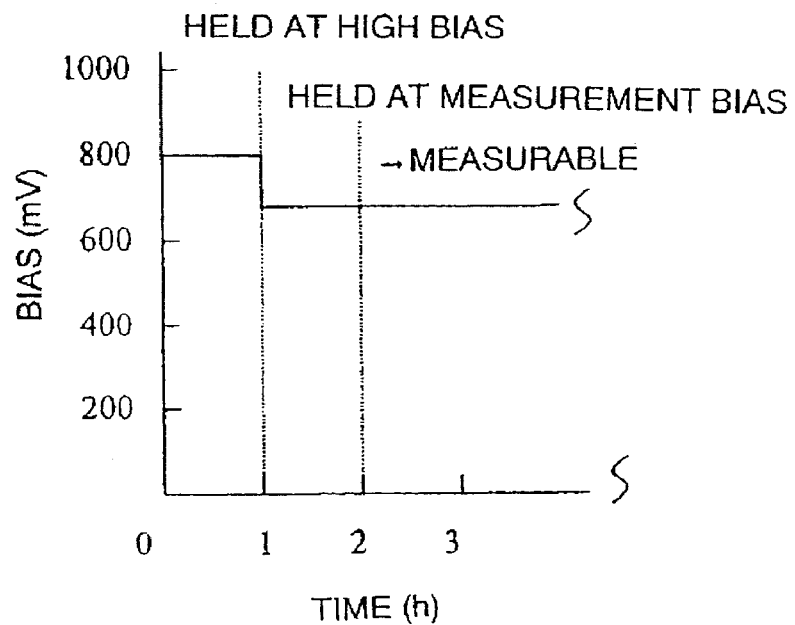
FIG. 3 is a bias chart showing one example in which an applied bias between a working electrode and a reference electrode of the chemical sensor in an initial treatment operation is set in the first embodiment of the present invention.

For the chemical sensor immersed in the buffer solution, a bias of 800 mV was applied to the working electrode 2 on the basis of the reference electrode 4, and the sensor was held for one hour. Next, the bias applied to the working electrode 2 was changed to 700 mV which was the measurement bias. After holding the sensor further for one hour, the measurement was started. FIG. 3 shows an applied bias chart with respect to the working electrode 2 at the time of the use start operation. When the chemical sensor subjected to the use start treatment was used to measure a glucose solution having a concentration of 50 mg/dl, 610 nA was obtained as a response current value. It is to be noted that for the enzyme electrode type chemical sensor, the response current value measured with respect to the glucose solution having a concentration of 50 mg/dl was 600 nA in a characteristic test performed before the drying/storing. On the next day, after holding the sensor in the standby state for 24 hours, the same measurement was repeated. After an elapse of one day, the measured response current value was 600 nA. Furthermore, the same measurement was repeated every day for three days, and the presence/absence of the change with the elapse of time was evaluated. As a result, the measured response current value underwent a change in a range of 590 to 610 nA.

For comparison, the glucose sensor having the same manufacturing lot number and stored in the dry state was immersed in the buffer solution. Thereafter, the same bias of 700 mV as the measurement bias was applied to the working electrode 2 on the basis of the reference electrode 4, and the sensor was held for two hours. When the chemical sensor subjected to the treatment was used to measure the glucose solution having a concentration of 50 mg/dl, 510 nA was obtained as the response current value. It is to be noted that also for this enzyme electrode type chemical sensor, the response current value measured with respect to the glucose solution having a concentration of 50 mg/dl was 600 nA in the characteristic test performed before the drying/storing. On the next day, after holding the sensor in the standby state for 24 hours, the same measurement was repeated. After the elapse of one day, the measured response current value was 580 nA. Furthermore, the same measurement was repeated every day for three days to evaluate the presence/absence of the change with the elapse of days. As a result, the measured response current value underwent a change in a range of 590 to 610 nA. That is, in the treatment in which after drying/holding the sensor and immersing the sensor in the buffer solution, the same bias of 700 mV as the measurement bias is applied to the working electrode 2 on the basis of the reference electrode 4 and the sensor is held for two hours, it has been found that the sensor sensitivity is significantly lower than an original level, and does not recover to the original level even after holding the sensor in the standby state for 24 hours in total. It is to be noted that the sensor sensitivity recovers to the original level in a stage in which the sensor is held in the standby state for 48 hours in total.

On the other hand, the glucose sensor disposed in the same manufacturing lot and stored in the dry state was subjected to the treatment in which the sensor was immersed in the buffer solution, a bias of 800 mV was applied to the working electrode 2 on the basis of the reference electrode 4, and the sensor was held for two hours. For the chemical sensor treated in this manner, the bias to be applied to the working electrode 2 was changed to 700 mV which was the measurement bias. After three minutes, the base current flowing between the working electrode 2 and the reference electrode 4 became constant. At this time, as a result of the measurement of the glucose sensor having a concentration of 50 mg/dl, a response current value of 720 nA was obtained. It is to be noted that also for this enzyme electrode type chemical sensor, the response current value measured with respect to the glucose solution having a concentration of 50 mg/dl was 600 nA in the characteristic test performed before the drying/storing. On the next day, after holding the sensor in the standby state for 24 hours, the same measurement was repeated. After the elapse of one day, the measured response current value was 600 nA. Furthermore, the same measurement was repeated every day for three days to evaluate the presence/absence of the change with the elapse of days. As a result, the measured response current value underwent a change in a range of 590 to 610 nA. That is, in the treatment in which after drying/holding the sensor and immersing the sensor in the buffer solution, a bias of 800 mV is applied to the working electrode 2 on the basis of the reference electrode 4 and the sensor is held for two hours, it has been found that the sensor sensitivity is significantly higher than the original level immediately after the treatment. However, thereafter when the bias to be applied to the working electrode 2 is changed to 700 mV which is the measurement bias, and the sensor is held in the standby state, it has been found that the sensor sensitivity is stabilized at the original level after the elapse of one day at latest.

Figure 4:
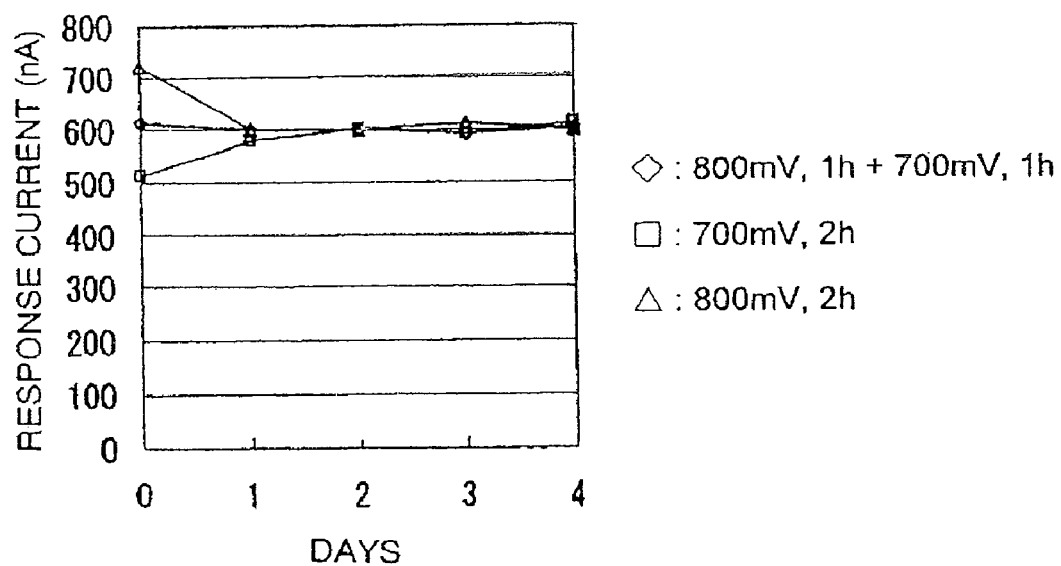
FIG. 4 is a graph for comparison of a difference of a change of a measurement result (response current) by the chemical sensor with an elapse of time, caused by initial treatment operation conditions at the stage of making first use of the chemical sensor in Example 1.

FIG. 4 shows the results of the evaluation of the changes of the sensor sensitivities (response current values) of the glucose sensor subjected to the above-described three types of treatment at the start of the use with the elapse of days in contrast to one another. Considering these results together, the following has been found. That is, during the storage in the standby state, the microscopic conditions of the surfaces of the working electrode and reference electrode of the enzyme electrode type chemical sensor shift to a state different from the state in which the measurement bias is applied and the sensor is immersed in the storage liquid for 24 or more hours. However, when the treatment of applying a bias significantly higher than the measurement bias and immersing and holding the sensor in the storage liquid is performed, the state of the electrode surface can recover to the originally stabilized state. It is to be noted that when the applied state of the high bias is changed to the usual measurement bias, the electric double layers caused by the charges accumulated on the electrode surface quickly change, and the base current flowing between the working electrode and the reference electrode becomes constant, but more time is required for stabilizing the electrostatically eccentric state in the whole enzyme electrode type chemical sensor. It is to be noted that it is judged that the sensor is sufficiently for one hour or less at longest in order to further stabilize the state depending on the change amount of the applied bias.

That is, it has been confirmed that the original sensor sensitivity of the enzyme electrode type chemical sensor can be stabilized in a short time, when the use start treatment operation is performed in accordance with the first measuring method of the present invention in order to start the use of the prepared enzyme electrode type chemical sensor stored in the dry state. After ending the use start treatment operation, the sensor sensitivity is stabilized. Even when sensitivity calibration is not performed for a specific period, the measurement satisfactory in precision and reproducibility can be carried out.

Moreover, for the setting of the applied bias and the condition of the holding time with respect to the measuring apparatus main body 9 for the enzyme electrode type chemical sensor, functions are added to software based on the above-described results. Accordingly, for hardware, a system for displaying that a series of use start treatment operation described above has been completed and that stable measurement is possible is also added.

For example, in the measuring apparatus main body 9 to which the above-described use start treatment operation function has been added, software change including bias application timing control and hardware change including addition of a detection system such as a lead switch for use in the control and an indicator portion of a measuring unit main body portion are made as follows.

After connecting the sensor in the dry state to the measuring apparatus main body 9, ①  the sensor is installed in a position where the sensor is immersed in the storage liquid (detected by the lead switch, and the like);

② the sensor is held for five minutes without applying the bias;

→This is because the film collapses when applying the bias in a state in which the whole organic film is not sufficiently wetted by the storage liquid.

③ the sensor is held at 750 mV for three hours;

④ the sensor is held at 450 mV for one hour; and

⑤ 450 mV is unchanged, but the indicator of the measuring unit main body portion indicates "measurable".

Second Embodiment

Figure 5:
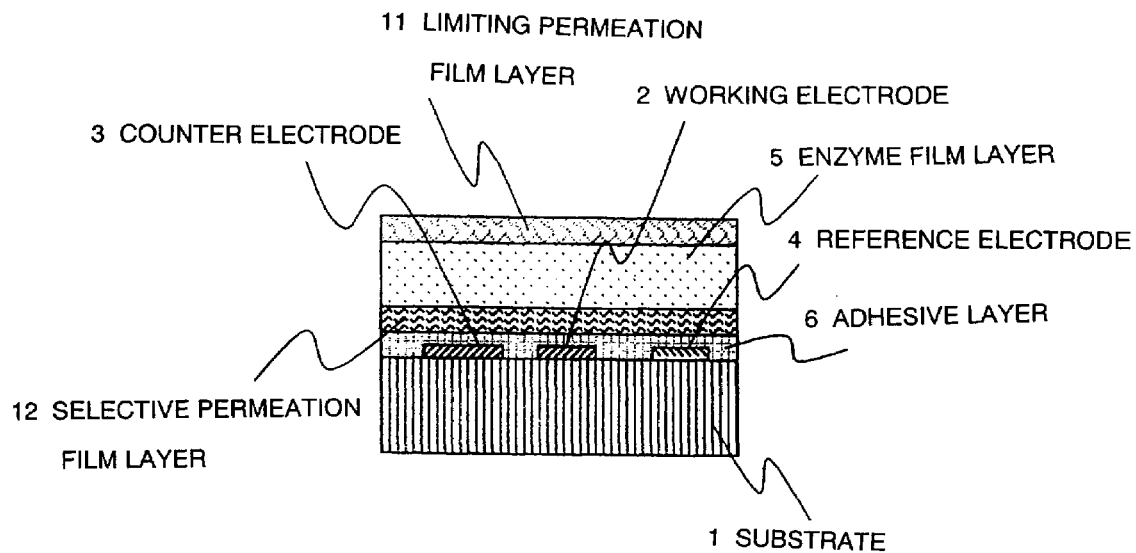
FIG. 5 is a sectional view schematically showing one example of the chemical sensor constitution using an enzyme electrode for use in a second embodiment of the present invention.

FIG. 5 is a sectional view schematically showing one example of a chemical sensor constitution for use in a second embodiment of the present invention. The chemical sensor shown in FIG. 2 is constituted of the chemical sensor including the three electrodes type, and the working electrode 2 and counter electrode 3 formed of conductors and the reference electrode 4 are formed on the insulating substrate 1. The enzyme film 5 is formed on the electrode system including the three electrodes type, and a so-called enzyme electrode type chemical sensor is constituted. It is to be noted that in the enzyme electrode, a limiting permeation film 11 is formed on the surface of the enzyme film 5, and a selective permeation film 12 is disposed on the electrode of the enzyme film 5. To immobilize these films, the adhesive layer 6 is disposed between the electrode system and the selective permeation film 12. The insulating substrate 1 does not indicate permeability to liquid, and the contact of the electrode system with the solution is achieved via the limiting permeation film 11, enzyme film 5, selective permeation film 12, and adhesive layer 6 which have the permeability to liquid. A concrete example of the enzyme electrode type chemical sensor using the enzyme electrode including the limiting permeation film on the outermost surface is disclosed, for example, in Japanese Patent No. 2943700.

The selective permeation film 12 participates in the electrochemical reaction in the electrode surface of the chemical sensor, and has a function of inhibiting permeation of the substance other than the final measurement object substance. This function is developed by a film structure in which the permeation of molecules having a large molecular weight is inhibited by a meshed structure or infiltration of ions is inhibited by an electrostatic repulsive force.

On the other hand, the limiting permeation film 11 limits permeability to the measurement object substance in the enzyme electrode. That is, when the permeability of the substrate material of the enzymatic reaction in the enzyme film 5 is lowered, and even when a substrate material concentration in the measurement sample is high, the amount of the substrate material reaching the enzyme film 5 per unit time can quantitatively be converted to a reaction product by an enzyme contained in the enzyme film 5. In general, when the amount of the substrate material reaching the enzyme film 5 is excessive, the amount of the reaction product converted by a limited amount of the enzyme contained in the enzyme film 5 per unit time has a certain upper limit, and quantitative property is lost between the substrate material amount and the reaction product amount. Then, a state referred to as sensor output saturation results. With the use of the constitution including the limiting permeation film 11 shown in FIG. 5, the concentration of the substrate material in the measurement sample reaching the sensor output saturation can remarkably be raised. That is, there is disposed a function of enlarging a concentration range, so-called dynamic range of the substrate material in the measurement sample measurable with high quantitative property. Furthermore, the limiting permeation film 11 has a function of limiting the permeability of not only the substrate material in the measurement sample but also various foreign substances contained in an actual measurement sample. Therefore, the film also performs a function of a chemical/physical protective film against various foreign substances which are factors for deterioration of the function of the enzyme film 5.

For example, the measurement sample solution which is the measurement object of the enzyme electrode type chemical sensor such as the glucose sensor contains various foreign substances other than the measurement object substance, such as blood, urine, and drainage. In the structure including only the enzyme film and electrode as shown in FIG. 3, the measurement sample is easily influenced, hindered, or interfered by these foreign substances, and a remarkable change of sensor performances is caused in rather many cases. When the selective permeation film 12 and limiting permeation film 11 are disposed, the enzyme electrode type chemical sensor can maintain stable performances and fulfill high quantitative property even in this strict environment.

However, in the structure in which the selective permeation film 12 and limiting permeation film 11 are disposed, desired permeation performances are secured with respect to low molecular seeds such as water of solvent, hydrogen peroxide molecules, and hydroxide ions ($OH^-$). However, the permeation performances are largely limited even with respect to ascorbic acid (vitamin C), soluble substance having a molecular size almost equal to that of glucose of the substrate, or ion seeds. Therefore, as compared with the structure including only the enzyme film and electrode as shown in FIG. 3, in the structure including the selective permeation film 12 and limiting permeation film 11 as shown in FIG. 5, for example, even when the surface coat layer existing on the surface of the working electrode 2 or the reference electrode 4 is transformed into the soluble substance, a time required for discharging the substance to the outside of the sensor from the vicinity of the surface of the working electrode 2 or the reference electrode 4 via the selective permeation film 12 or the limiting permeation film 11 tends to lengthens.

Even in the enzyme electrode type chemical sensor including the structure shown in FIG. 5, to start the use of the sensor stored in the dry state in accordance with the first measuring method of the present invention, in the first initial treatment step, an applied bias selected at a value significantly larger than the measurement bias, for example, by at least 100 mV and in a range which does not exceed 900 mV is applied between the working electrode 2 and reference electrode 4 formed of the platinum electrode on the basis of the silver/silver chloride electrode constituting the reference electrode in the buffer solution for use in the storage liquid. When the chemical sensor is held, it is possible to quickly remove the surface coat layer existing on the surfaces of the working electrode 2 or the reference electrode 4. It is to be noted that a preferable range of the first initial treatment bias applied between the working electrode 2 and reference electrode 4 in the first initial treatment step in the structure including only the enzyme film and electrode as shown in FIG. 3 is essentially the same as that in the structure including the selective permeation film 12 and limiting permeation film 11 shown in FIG. 5 as long as the storage liquid for use and the conductive materials of the working electrode 2 and reference electrode 4 are the same. Furthermore, a time required for transforming the surface coat layer existing on the surfaces of the working electrode 2 and reference electrode 4 into the soluble substance to discharge the substance to the outside of the sensor via the selective permeation film 12 or the limiting permeation film 11 is long as compared with the structure including only the enzyme film and electrode as shown in FIG. 3. However, this first initial treatment time can be set in such a range that does not exceed four hours.

On the other hand, thereafter, a time (second initial treatment time) for changing the applied bias and applying/holding the second initial treatment bias (measurement bias) is preferably set to be gradually long as the bias change amounts of the first initial treatment bias and the second initial treatment bias (measurement bias) increase even in the enzyme electrode type chemical sensor structured as shown in FIG. 5. However, for the bias change, the bias application direction is not reversed, the bias change amount is about 500 mV at most, and the stable state can sufficiently be achieved in a second initial treatment time of one hour or less.

It is to be noted that to start the use of the sensor stored in the dry state even in the structure including the selective permeation film 12 and limiting permeation film 11 shown in FIG. 5, the same bias as the measurement bias is applied between the working electrode 2 and the reference electrode 4 in the buffer solution for use as the storage liquid, and the sensor is held for a long duration. Then, the sensor sensitivity gradually recovers to the original sensitivity, but the time required for the recovery process is not less than one day. Depending on the circumstances, after the elapse of a few days, the original sensor sensitivity is gradually stabilized. On the other hand, in the structure including the selective permeation film 12 and limiting permeation film 11 shown in FIG. 5, as compared with the structure including only the enzyme film and electrode as shown in FIG. 3, a long duration is required. However, when the initial treatment operation is performed in accordance with the first measuring method of the present invention, a period for achieving the stabilization onto the original sensor sensitivity can remarkably be reduced to six hours or less at longest as compared with a case where any initial treatment operation is not performed.

EXAMPLE 2

A glucose sensor constituted as shown in FIG. 5 was used as the enzyme electrode type chemical sensor in Example 2. The electrode system of the enzyme electrode type chemical sensor was set to the three electrodes type constituted of the working electrode 2 and counter electrode 3 of Pt, and the reference electrode 4 of Ag/AgCl. The enzyme film 5 was an immobilized enzyme film obtained by immobilizing glucose oxidase in the matrix of albumin and glutaric aldehyde. The silane coupling agent was disposed as the adhesive layer 6 on the electrode. The selective permeation film 12 formed of an ion exchange resin, and enzyme film 5 were disposed, and the outermost surface was coated with the limiting permeation film 11 formed of a fluoric resin. The enzyme electrode type chemical sensor was sealed in the cartridge 7 formed of plastic in the liquid-tight manner and was used. The window 8 was disposed in the cartridge 7 so that only the sensitive portion of the glucose sensor contacts the solution.

In the sensor in which the limiting permeation film 11 is disposed, the range of the concentration of measurable glucose is expanded. Therefore, the measurement with high quantitative property is possible even without subjecting the sample solution indicating various glucose concentrations to a diluting operation beforehand to adjust the glucose concentration. Moreover, by the function of the selective permeation film 12, hydrogen peroxide which is an enzymatic reaction product generated from substrate glucose passes through the selective permeation film 12, but is not easily influenced by the other interfering substances such as ascorbic acid (vitamin C).

When the method of the initial treatment operation of the present invention was applied in the same manner as in Example 1, the conditions were optimized. As a result of the study on the conditions, the following has been found. When a bias of 450 mV is applied as the measurement bias to the working electrode 2 on the basis of the reference electrode 4, a bias of 750 mV is applied as the first initial treatment bias to the working electrode 2 on the basis of the reference electrode 4, and the sensor is held for four hours which is the first initial treatment time. Next, the bias applied to the working electrode 2 is changed to 450 mV, and the sensor is held for one hour which is the second initial treatment time. Thereafter, when the measurement is started, the sensor sensitivity is stabilized at the original sensitivity with a high reproducibility. When the glucose solution having a concentration of 500 mg/dl was measured, a response current value of 100 nA was obtained. It is to be noted that for the enzyme electrode type chemical sensor, the response current value measured with respect to the glucose solution having a concentration of 500 mg/dl was 100 nA in the characteristic test performed before the drying/storing. Furthermore, after four days, the same measurement was repeated every day to evaluate the presence/absence of the change with the elapse of days. Then, the measured response current value underwent a change in a range of 100 nA±5 nA.

For comparison, the glucose sensor having the same manufacturing lot number and stored in the dry state was immersed in the buffer solution. Thereafter, the same bias of 450 mV as the measurement bias was applied to the working electrode 2 on the basis of the reference electrode 4, the glucose solution having a concentration of 50 mg/dl was measured, and the initial response current value was less than 40 nA. It is to be noted that also for this enzyme electrode type chemical sensor, the response current value measured with respect to the glucose solution having a concentration of 50 mg/dl was 100 nA in the characteristic test performed before the drying/storing. Furthermore, after four days, the same measurement was repeated every day to evaluate the presence/absence of the change with the elapse of days. After the elapse of one day, the measured response current value recovered to 80 nA. However, it has been confirmed that the sensor sensitivity is finally stabilized at the original value.

Figure 6:
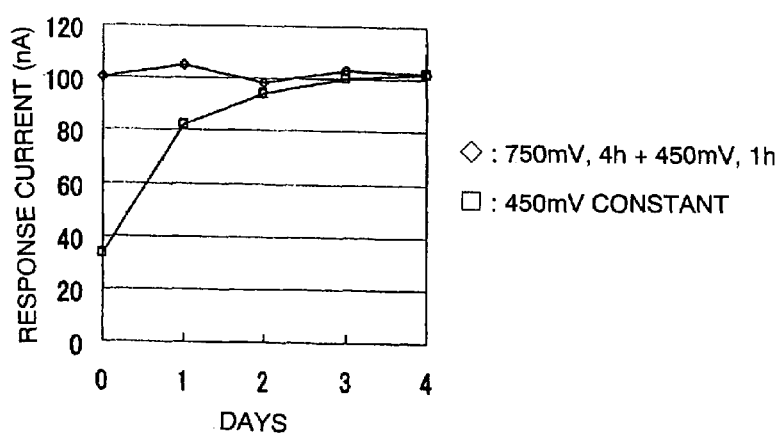
FIG. 6 is a graph for comparison of the difference of the change of the measurement result (response current) by the chemical sensor with the elapse of time, caused by the initial treatment operation conditions at the stage of making first use of the chemical sensor in Example 2.

FIG. 6 shows the results of the evaluation of the changes of the sensor sensitivities (response current values) of the glucose sensor subjected to the above-described two types of treatment at the start of the use with the elapse of days in comparison with one another. By this comparison, it has been judged that the initial treatment method at the start of the use in accordance with the first measuring method of the present invention is more advantageous in the enzyme electrode type chemical sensor including the structure including the selective permeation film 12 and limiting permeation film 11 shown in FIG. 5

Third Embodiment

It has been found that when the enzyme electrode type chemical sensor constituted to include the selective permeation film 12 and limiting permeation film 11 shown in FIG. 5 is subjected to the initial treatment operation described in the second embodiment, a stable sensor sensitivity is obtained from the start of the use, but the sensor sensitivity gradually drops after the use for a long duration.

The drop of the sensor sensitivity seen in the use for a long period is considered to be caused, for example, by the adsorption of the interference substance onto the surface of the chemical sensor or the electrode, which is one factor, with the repeated measurement. However, the present inventors have found that the sensor sensitivity similarly drops with the elapse of time, even when the measurement bias is applied and the sensor is held in the storage liquid (held in the standby state) without performing the measurement. That is, it has been revealed that the surface coat layer is slowly formed on the electrode surface, which causes a certain drop of the sensor sensitivity, during the application of the measurement bias and the leaving of the sensor in the buffer solution (the holding in the standby state), even when various interference substances do not exist in the actual measurement sample.

Against the drop of the sensor sensitivity caused by the adsorption of the interference substances onto the surface of the chemical sensor or the surface of the electrode, various reactivating treatments of the enzyme electrode described above can be used. However, for an internal factor that is the formation of the surface coat layer in the buffer solution for use in the storage liquid instead of an external factor that is the interference substance, a refresh treatment operation in accordance with a second measuring method of the present invention is effective.

Concretely, every use for a predetermined period, the chemical sensor in the standby state is subjected to a first refresh treatment step of applying a first refresh treatment bias having the same direction as that of the measurement bias and possessing an absolute value larger than that of the measurement bias between the working electrode and the reference electrode, and holding the chemical sensor for a predetermined first refresh treatment time. After ending the first refresh treatment step, a refresh standby treatment step is performed in which the bias applied between the working electrode and the reference electrode is changed to a second refresh treatment bias that is the same as the measurement bias, and the chemical sensor is held in the standby state for a second refresh treatment time. Accordingly, the sensor sensitivity drop by the internal factor is recovered.

The first refresh treatment bias for use in the refresh treatment is preferably selected in a range similar to that of the first initial treatment bias for use in the initial treatment at the start of the use. That is, both preferable ranges agree with each other. On the other hand, the first refresh treatment time can remarkably be shortened as compared with the first initial treatment time. Concretely, a first refresh treatment time of about one hour can be selected. On the other hand, the second refresh treatment time is a time required for solving the electrostatic change accompanying the change of the applied bias, and may essentially be selected in a range similar to that of the second initial treatment time. It is to be noted that since the first refresh treatment time is much shorter than the first initial treatment time, there is no problem, even when the second refresh treatment time is set to be slightly shorter than the second initial treatment time, for example, about 30 minutes.

The refresh treatment operation in accordance with the second measuring method of the present invention is performed for a purpose of recovering the sensor sensitivity drop by the internal factor. Different from the conventional reactivating treatment technique of the enzyme electrode for performing the treatment every measurement for a purpose of recovering the sensor sensitivity drop caused by the external factor of the interference substances generated from the measurement sample, depending on the number of measurements to be performed, the refresh operation is effectively periodically incorporated in the operation in accordance with the second measuring method. When the refresh operation is periodically performed, the sensor sensitivity drop by the internal factor is recovered, and the initial sensor sensitivity can be maintained for a long duration.

EXAMPLE 3

Ten glucose sensors including the same structure as that of Example 2 were used to periodically measure control urine having a nominal glucose concentration of 280 mg/dl (abnormal manufactured by Baio Rad Co.) over two months. The ten sensors were divided into groups each including five sensors. For one of the groups, the refresh treatment was performed once a week. A bias of 750 mV higher than the measurement bias was applied to the working electrode 2 on the basis of the reference electrode 4. After holding the sensors for 30 minutes, the bias to be applied to the working electrode 2 was changed to the same bias of 450 mV as the measurement bias, and the measurement was performed after the elapse of 30 minutes or more. On the other hand, the other group was not subjected to the refresh treatment, and the same constant bias of 450 mV as the measurement bias was continuously applied to the working electrode 2 even during the standby state.

Figure 7:
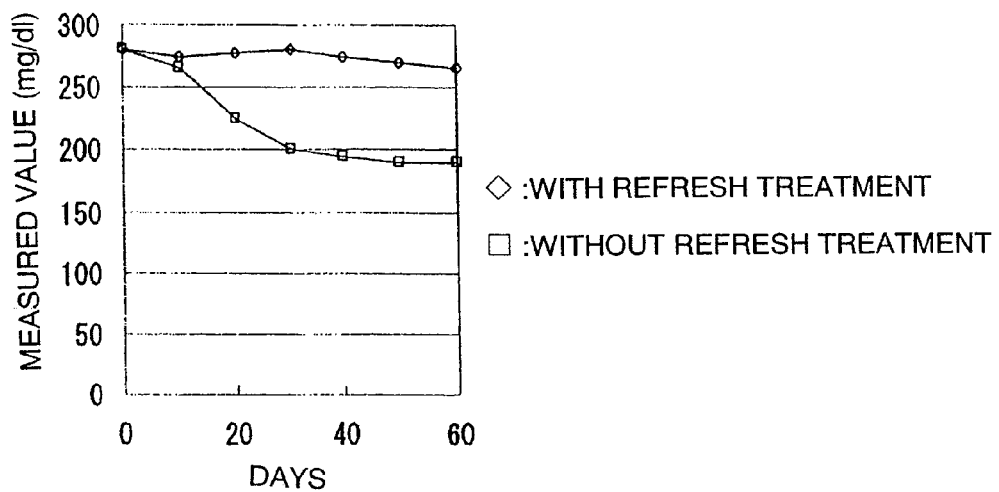
FIG. 7 is a graph for comparison of the difference of the change of the measurement result (response current) by the chemical sensor with the elapse of time, caused by presence/absence of a periodic refresh treatment operation by the present invention after making first use of the chemical sensor in Example 3.
Figure 8:
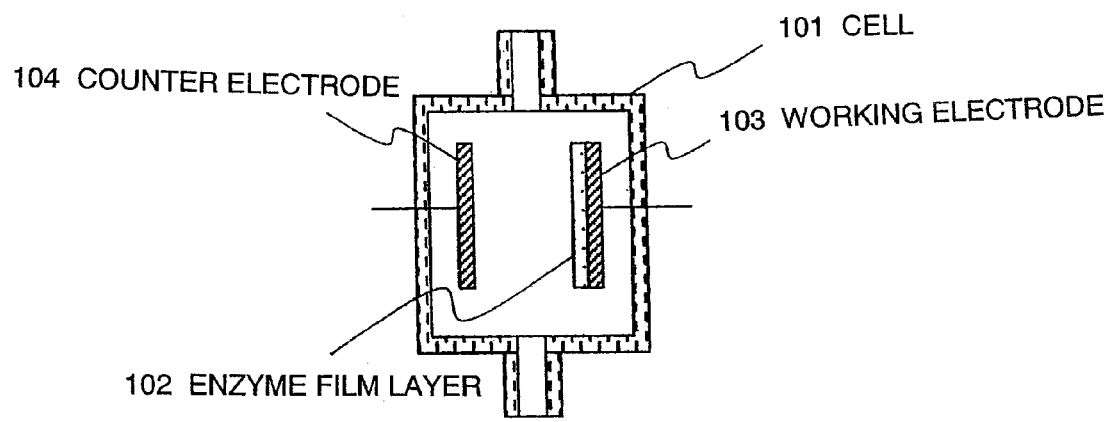
FIG. 8 is a sectional view showing a constitution example of a conventional cell type chemical sensor in which a working electrode including an enzyme film layer is disposed separately from a counter electrode.
Figure 9:
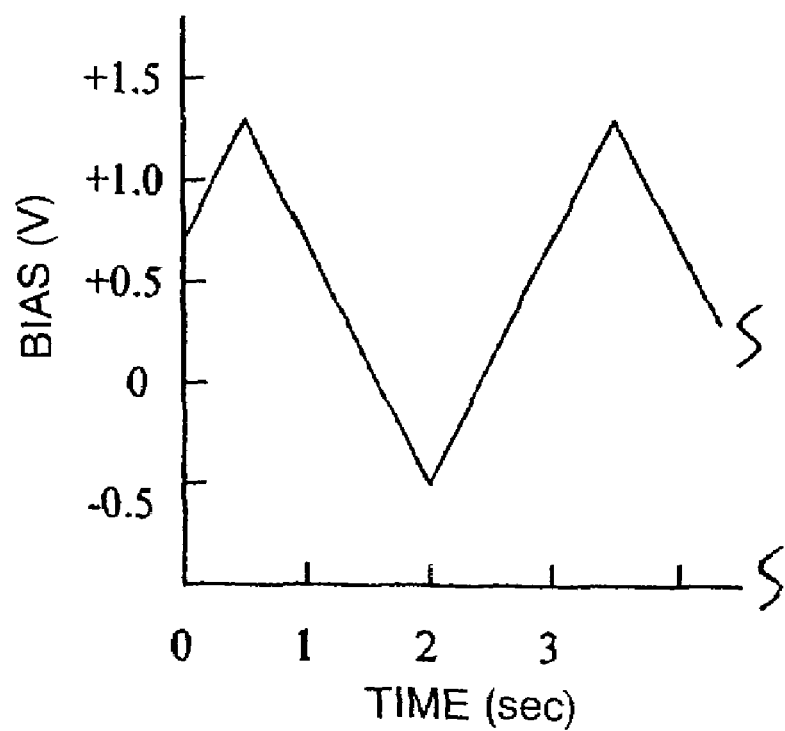
FIG. 9 is a bias chart showing one example of applied bias sweeping between the working electrode and reference electrode of the chemical sensor for use in an enzyme electrode activation method of a triangular wave bias sweeping system.

For these two groups, the changes of the results of the periodic measurement of the control urine with the elapse of time were compared. FIG. 7 shows one example of the comparison result. Both in the groups, a slight scattering is seen in each sensor, but the tendencies of the changes with the elapse of time in the groups agree with each other. That is, in the group subjected to the periodic refresh treatment, substantially the same measured value is obtained in this period, and the sensor sensitivity is maintained. On the other hand, in the group in which any refresh treatment is not performed, the measured value drops with an elapse of time, and turns to be ⅔ of the initial measured value after two months.

It is to be noted that the presence of the sensor sensitivity drop by the internal factor caused only by the holding of the standby state in the buffer solution for use in the storage liquid has separately been confirmed in addition to the sensor sensitivity drop by the interference substances constituting the external factor accompanying the periodic measurement of the control urine. Even when the sensor sensitivity drops by the internal factor, the sensor sensitivity is recovered to the original level by the refresh treatment performed on the above-described conditions.

From the above-described result, the refresh treatment operation in accordance with the second measuring method of the present invention is effective for reactivation of the enzyme electrode, even when the sensor sensitivity drops by the interference substances constituting the external factor accompanying the periodic measurement of the control urine. Additionally, it is judged that it is optimum to periodically perform the refresh treatment regardless of the presence/absence of the measurement in order to maintain the sensor sensitivity over a long period.

From the above-described standpoint, with respect to the measuring apparatus main body 9 for the enzyme electrode type chemical sensor, the functions for the setting of the applied bias and the conditions of the holding time have been added to software in order to automatically perform the refresh treatment operation, when the number of measurements exceeds a predetermined number or after the elapse of a predetermined time. Accordingly, the system for displaying that the series of refresh treatment operation is completed and the stable measurement is possible has also been added to hardware.

INDUSTRIAL APPLICABILITY

As explained above, according to the present invention, initial performances of the chemical sensor can be maintained over a long period. Moreover, since any special standby time is not required excluding the time immediately after the refresh operation, the measurement can repeatedly be performed usually at a short interval.

Additionally, according to the present invention, the performances of the enzyme electrode maintained in the dry state for a long duration can quickly be returned to the performances immediately after the preparation. Since the sensitivity can always be constant, it is possible to perform the measurement with good precision over a long period substantially without performing any calibration. It is also possible to repeatedly perform the measurement at a short interval as compared with the prior art.

The invention claimed is:

1. A method of measuring a concentration of a specific substance contained in a measurement sample by use of a chemical sensor comprising at least a working electrode and a reference electrode, wherein the method is a measurement method according to such a procedure that the chemical sensor is immersed into a buffer solution of a predetermined composition used as a storage liquid during standby, and a predetermined measurement bias is applied between the working electrode and the reference electrode to hold the chemical sensor in the buffer solution, and the chemical sensor is immersed into the measurement sample instead of the buffer solution, and the measurement bias applied between the working electrode and the reference electrode is used to measure the concentration of the specific substance contained in the measurement sample based on a change in an amount of a current produced by an electrochemical reaction during measurement; and the method comprising the following procedure for initial treatment, at the stage of making first use of the chemical sensor:

as a first bias application after immersing the chemical sensor kept under a dry state into the buffer solution to bring the surfaces of the working electrode and reference electrode into contact with the buffer solution, a first initial treatment step of applying a first initial treatment bias having the same direction as that of the measurement bias and possessing an absolute value larger than that of the measurement bias between the working electrode and the reference electrode to hold the chemical sensor in the buffer solution for a predetermined first initial treatment time;

a second initial treatment step of changing the bias to be applied between the working electrode and the reference electrode to a second initial treatment bias which is the same as the measurement bias, after ending the first initial treatment step, while the chemical sensor is immersed in the buffer solution, and holding the chemical sensor in a standby state; and after the completion of the second initial treatment step, the chemical sensor is placed for the first time at the use for measurement of the measurement sample, wherein any bias applied between the working electrode and the reference electrode during said procedure for initial treatment has the same direction as that of the measurement bias.

2. The method according to claim 1, wherein, after ending the first initial treatment step, in the second initial treatment step, the chemical sensor is held in the standby state for a predetermined second initial treatment time.

3. The method according to claim 2, wherein the chemical sensor further comprises a counter electrode, the working electrode, and the reference electrode, the counter electrode in addition to the working electrode and the reference electrode, the reference electrode is constituted of a material having a predetermined chemical potential difference from the working electrode, when brought into contact with the buffer solution, the reference electrode is used as a reference to set the bias for the working electrode in such a manner that a desired bias is applied between the working electrode and the reference electrode in the steps of applying the measurement bias, the first initial treatment bias, and the second initial treatment bias, and the steps of applying the measurement bias, the first initial treatment bias, and the second initial treatment bias are set respectively in such a manner that the difference between the biases of the reference electrode and working electrode in the buffer solution imparts the bias difference in accordance with the measurement bias, the first initial treatment bias, and the second initial treatment bias.

4. The method according to claim 3, wherein a silver/silver chloride electrode is used as the reference electrode, and a platinum electrode is used for the working electrode and the counter electrode, and said measurement bias applied between the working electrode and the reference electrode during the measurement is an applied bias obtained by the bias of the working electrode selected from a range of 400 to 700 mV on the datum basis of the silver/silver chloride electrode used as the reference electrode in the buffer solution.

5. The method according to claim 4, wherein in the first initial treatment step, the first initial treatment bias applied between the working electrode and the reference electrode is selected in a range of the applied bias which is larger than the measurement bias by at least 100 mV or more and which does not exceed 900 mV on the datum basis of the silver/silver chloride electrode used as the reference electrode in the buffer solution.

6. The method according to claim 5, wherein said chemical sensor is an amperometric chemical sensor, wherein the working electrode, counter electrode, and reference electrode are all formed on an insulating substrate, and an enzyme electrode comprising at least an immobilized enzyme film layer disposed on the surface of the working electrode is used for the current detection.

7. The method according to claim 4, wherein in the first initial treatment step, the first initial treatment bias applied between the working electrode and the reference electrode is selected in a range of at least 750 mV to 900 mV on the datum basis of the silver/silver chloride electrode used as the reference electrode in the buffer solution, and the first initial treatment time is selected in a range of four hours or less and at least not less than one hour.

8. The method according to claim 7, wherein said chemical sensor is an amperometric chemical sensor, wherein the working electrode, counter electrode, and reference electrode are all formed on an insulating substrate, and an enzyme electrode comprising at least an immobilized enzyme film layer disposed on the surface of the working electrode is used for the current detection.

9. The method according to claim 4, wherein said second initial treatment time is selected at least in a range of not less than one hour.

10. The method according to claim 9, wherein a total of the first initial treatment time and the second initial treatment time is selected in a range of six hours or less.

11. The method according to claim 10, wherein said chemical sensor is an amperometric chemical sensor, wherein the working electrode, counter electrode, and reference electrode are all formed on an insulating substrate, and an enzyme electrode comprising at least an immobilized enzyme film layer disposed on the surface of the working electrode is used for the current detection.

12. The method according to claim 9, wherein said chemical sensor is an amperometric chemical sensor, wherein the working electrode, counter electrode, and reference electrode are all formed on an insulating substrate, and an enzyme electrode comprising at least an immobilized enzyme film layer disposed on the surface of the working electrode is used for the current detection.

13. The method according to claim 4, wherein in the first initial treatment step, an applied bias at which an electrolysis reaction of water starts on the working electrode and the counter electrode in the buffer solution is defined as an applied bias upper limit value, and the measurement bias is defined as an applied bias lower limit value on the datum basis of the silver/silver chloride electrode used as the reference electrode, respectively; and by using an upper/lower limit bias difference defined by a difference between the applied bias upper and lower limit values, the first initial treatment bias applied between the working electrode and the reference electrode is selected in a range of the applied bias which is larger than the measurement bias by 10% or more of the upper/lower limit bias difference and which is smaller than the applied bias upper limit value by at least 200 mV or more.

14. The method according to claim 4, wherein said chemical sensor is an amperometric chemical sensor, wherein
the working electrode, counter electrode, and reference electrode are all formed on an insulating substrate, and
an enzyme electrode comprising at least an immobilized enzyme film layer disposed on the surface of the working electrode is used for the current detection.

15. The method according to claim 3, wherein in the first initial treatment step,
an applied bias at which an electrolysis reaction of water starts on the working electrode and the counter electrode in the buffer solution is defined as an applied bias upper limit value, and the measurement bias is defined as an applied bias lower limit value on the datum basis of the silver/silver chloride electrode used as the reference electrode, respectively; and
by using an upper/lower limit bias difference defined by a difference between the applied bias upper and lower limit values, the first initial treatment bias applied between the working electrode and the reference electrode is selected in a range of the applied bias which is larger than the measurement bias by 10% or more of the upper/lower limit bias difference and which is smaller than the applied bias upper limit value by at least 200 mV or more.

16. The method according to claim 5, wherein said chemical sensor is an amperometric chemical sensor, wherein
the working electrode, counter electrode, and reference electrode are all formed on an insulating substrate, and
an enzyme electrode comprising at least an immobilized enzyme film layer disposed on the surface of the working electrode is used for the current detection.

17. The method according to claim 3, wherein said chemical sensor is an amperometric chemical sensor,
wherein the working electrode, counter electrode, and reference electrode are all formed on an insulating substrate, and
an enzyme electrode comprising at least an immobilized enzyme film layer disposed on the surface of the working electrode is used for the current detection.

18. A method of measuring a concentration of a specific substance contained in a measurement sample by use of a chemical sensor having at least a working electrode and a reference electrode, wherein the method is a measurement method according to such a procedure that the chemical sensor is immersed into a buffer solution of a predetermined composition used as a storage liquid during standby, and a predetermined measurement bias is applied between the working electrode and the reference electrode to hold the chemical sensor in the buffer solution, and the chemical sensor is immersed into the measurement sample instead of the buffer solution, and the measurement bias applied between the working electrode and the reference electrode is used to measure the concentration of the specific substance contained in the measurement sample based on a change in an amount of a current produced by an electrochemical reaction during measurement; and the method comprising the following procedure for refresh treatment, at every stage post to continued use of the chemical sensor for a predetermined period, as a first bias application in a condition in which the chemical sensor in a standby state is immersed in the buffer solution, and the surfaces of the working electrode and reference electrode are allowed to contact the buffer solution;

a first refresh treatment step of applying a first refresh treatment bias having the same direction as that of the measurement bias and possessing an absolute value larger than that of the measurement bias between the working electrode and the reference electrode, and holding the chemical sensor in the buffer solution for a predetermined first refresh treatment time;

a refresh standby treatment step of changing the bias applied between the working electrode and the reference electrode to a second refresh treatment bias which is the same as the measurement bias, after ending the first refresh treatment step, while the chemical sensor is immersed in the buffer solution, and holding the chemical sensor in a standby state for a second refresh treatment time; and after completion of the refresh standby treatment step, the chemical sensor is placed again at the use for the measurement of the measurement sample, wherein any bias applied between the working electrode and the reference electrode during said procedure for refresh treatment has the same direction as that of the measurement bias.

* * * * *

UNITED STATES PATENT AND TRADEMARK OFFICE
CERTIFICATE OF CORRECTION

PATENT NO.      : 7,641,784 B2  
APPLICATION NO. : 10/766068  
DATED           : January 5, 2010  
INVENTOR(S)     : Saito et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1159 days.

Signed and Sealed this

Twenty-first Day of December, 2010

David J. Kappos  
*Director of the United States Patent and Trademark Office*